United States Patent
Nitz et al.

(10) Patent No.: US 6,495,580 B1
(45) Date of Patent: Dec. 17, 2002

(54) COMPOUNDS, COMPOSITIONS AND METHODS FOR TREATING OR PREVENTING PNEUMOVIRUS INFECTION AND ASSOCIATED DISEASES

(75) Inventors: Theodore J. Nitz, Pottstown; Daniel C. Pevear, Harleysville, both of PA (US)

(73) Assignee: ViroPharma Incorporated, Exton, PA (US)

(*) Notice: Subject to any disclaimer, the term of this patent is extended or adjusted under 35 U.S.C. 154(b) by 0 days.

(21) Appl. No.: 09/254,690

(22) PCT Filed: Jan. 29, 1999

(86) PCT No.: PCT/US99/01985

§ 371 (c)(1),
(2), (4) Date: Oct. 18, 1999

(87) PCT Pub. No.: WO99/38508

PCT Pub. Date: Aug. 5, 1999

Related U.S. Application Data

(60) Provisional application No. 60/073,038, filed on Jan. 29, 1998, and provisional application No. 60/073,078, filed on Jan. 30, 1999.

(51) Int. Cl.⁷ ......................... C07D 207/30; A61K 31/33
(52) U.S. Cl. ......................... 514/365; 514/378; 514/381; 514/383; 514/348; 548/203; 548/247; 548/251; 548/252; 548/265.2; 548/336.1
(58) Field of Search ................ 548/251, 252, 548/203, 247, 265.2, 336.1; 514/381, 398, 378, 365, 383

(56) References Cited

U.S. PATENT DOCUMENTS

| | | | |
|---|---|---|---|
| 3,954,398 A | * | 5/1976 | Ramanathan ................ 8/41 |
| 4,308,382 A | | 12/1981 | Zenith |
| 4,324,794 A | | 4/1982 | Tidwell et al. |
| 4,943,574 A | | 7/1990 | Raeymaekers et al. |
| 5,098,920 A | | 3/1992 | Reitz |
| 5,227,429 A | * | 7/1993 | Kawamura ................ 525/92 |
| 5,773,646 A | | 6/1998 | Chandrakumar et al. |

FOREIGN PATENT DOCUMENTS

| | | |
|---|---|---|
| EP | 0 795 549 A1 | 9/1997 |
| GB | 1 508 391 | 4/1978 |
| JP | 60-237047 | 11/1985 |
| WO | WO 95/00131 | 1/1995 |
| WO | WO 97/05125 | 2/1997 |
| WO | WO 01/00611 A1 | 1/2001 |
| WO | WO 01/00612 A2 | 1/2001 |
| WO | WO 01/00615 A1 | 1/2001 |

OTHER PUBLICATIONS

Abstract/Poster presented by T.J. Nitz at the 40ᵗʰ Interscience Conference on Antimicrobial Agents and Chemotherapy (at Toronto, Ontario) on Sep. 16, 2000.

Schlegel, D.C. et al. "Bulky Amine Analogues of Ketoprofen: Potent Antiinflammatory Agents"; J. Med. Chem. 27: 1690–1701 (1984).

Baker, B.R. et al. "Irreversible Enzyme Inhibitors. 181. Inhibition of Brain Choline Acetyltransferase by Derivatives of 4–Stilbazole"; J. Med. Chem. 14(4): 315–322 (1971).

DeClercq, E. "Perspectives for the chemotherapy of respiratory Syncytial virus (RSV) infections"; International Journal of Antimicrobial Agents 7: 193–202 (1996).

* cited by examiner

*Primary Examiner*—Robert Gerstl
(74) *Attorney, Agent, or Firm*—Dann Dorfman Herrell and Skillman, P.C.

(57) ABSTRACT

Compounds, compositions and methods are provided for the prophylaxis and treatment of infections caused by viruses of the Pneumovirinae subfamily of Paramyxoviridae and diseases associated with such infections.

38 Claims, No Drawings

COMPOUNDS, COMPOSITIONS AND METHODS FOR TREATING OR PREVENTING PNEUMOVIRUS INFECTION AND ASSOCIATED DISEASES

CROSS-REFERENCE TO RELATED APPLICATIONS

The present application is the U.S. National Phase of International Application No. PCT/US99/01985, filed Jan. 29, 1999, which claims the benefit of U.S. Provisional Application Nos. 60/073,038, filed Jan. 29, 1998 and 60/073,078, filed Jan. 30, 1998.

FIELD OF THE INVENTION

The present invention relates to compounds, compositions and methods for preventing and treating viral infections, and the diseases associated therewith, particularly those viral infections and associated diseases caused by viruses of the Pneumovirinae subfamily of the Paramyxoviridae.

BACKGROUND OF THE INVENTION

The Pneumovirinae subfamily of the Paramyxoviridae family consists of pneumoviruses that cause significant disease in humans and a number of animal species including cattle, goats, sheep, mice and in avian species.

Human respiratory syncytial virus (RSV), the prototypic member of the pneumovirus group, is the major pediatric viral respiratory tract pathogen, causing pneumonia and bronchiolitis in infants and young children. RSV disease is seasonal, with outbreaks in the U.S. typically beginning in November and continuing through April. During these yearly epidemics, approximately 250,000 infants contract RSV pneumonia, and up to 35% are hospitalized. Of those hospitalized, mortality rates of up to 5% have been reported. Children with underlying conditions such as prematurity, congenital heart disease, bronchopulmonary dysplasia and various congenital or acquired immunodeficiency syndromes are at greatest risk of serious RSV morbidity and mortality. In adults, RSV usually causes upper respiratory tract manifestations but can also cause lower respiratory tract disease, especially in the elderly and in immunocompromised persons. Infection in elderly and immunocompromised persons can be associated with high death rates. Natural infection with RSV fails to provide full protective immunity. Consequently, RSV causes repeated symptomatic infections throughout life.

The pneumoviruses of animals and avian species are similar to the human virus antigenically, in polypeptide composition and in disease causation.

Attempts to develop vaccines for RSV are ongoing, but none have yet been demonstrated to be safe and efficacious. Vaccine development has been shadowed by adverse reactions exhibited by the initial formalin-inactivated RSV vaccine introduced in the late 1960s. Immunized children showed an increased incidence of RSV lower respiratory tract disease and developed abnormally severe illnesses, including death.

Chemotherapy with ribavirin [1-beta-D-ribofuranosyl-1H-1,2,4-triazole-3-carboxamide], an antiviral nucleoside which is the only pharmaceutical approved by the U.S. Food and Drug Administration (FDA) for treatment of RSV disease, is considered only for certain RSV patients (e.g., those at high risk for severe complications or who are seriously ill with this infection). However, its efficacy and value are controversial. Recent studies have reported a failure to demonstrate either clinical or economic benefit to patients of ribavirin treatment. Moreover, ribavirin has certain toxic side-effects and, in order to minimize these, must be administred by inhalation as an aerosol in an enclosed environment.

A human intravenous immune globulin (IVIG) preparation is licensed for prophylactic use in certain patients at high-risk for RSV disease. Administration of this drug requires intravenous infusion of a large volume over a 2 to 4 hour period in children who have limited venous access due to prior intensive therapy, as well as compromised cardiopulmonary function. Moreover, intravenous infusion necessitates monthly hospital visits during the RSV season, which in turn places children at risk of nosocomial infections.

Thus, a need exists for new anti-viral agents and treatments for RSV infection that overcome the shortcomings of existing pharmaceutical preparations.

SUMMARY OF THE INVENTION

In one aspect, the invention provides a compound of the formula:

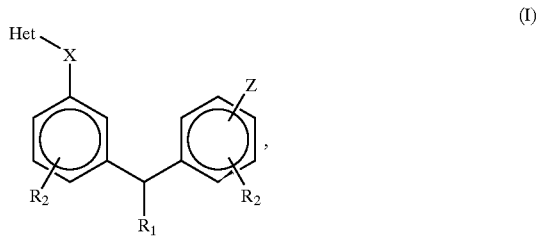

(I)

wherein Het represents an unsubstituted or substituted five to seven membered heterocyclic ring containing one to three heteroatoms selected from nitrogen, oxygen or sulfur, said heterocyclic ring substituents being at least one selected from those consisting of hydrogen, alkyl, amino, monoalkylamino or dialkylamino;

$R_1$ represents a radical selected from the group consisting of hydrogen; halogen; perfluoroalkyl; alkoxyalkyl; amino; alkylamino; dialkylamino; amido; alkylaminoalkyl; an unsubstituted or substituted, saturated or unsaturated, straight- or branched-chain alkyl radical, said alkyl chain substituent being at least one hydroxy group; carboxy; an unsubstituted or substituted phenyl radical ($C_6H_5$), said phenyl radical substituent being at least one selected from the group consisting of hydroxy, alkoxy, alkoxyalkyl, halogen, perfluoroalkyl, thio, nitro, carboxy, carboxyalkyl, carbalkoxy, carbalkoxyalkyl, carboxamide, carboxamidoalkyl, alkyl, cycloalkyl, alkylthio, alkylsulfinyl, alkylsulfonyl, sulfonamide, amidino, cyano, amino, amido, alkylamino, dialkylamino, alkylaminoalkyl, or alkoxy monosubstituted with a substituent selected from the group consisting of carboxy, amino, alkylamino or dialkylamino; a cycloalkyl radical; or a heterocyclic radical selected from the group consisting of pyridine, thiophene, oxazole, oxadiazole, thiadiazole, pyrazole, tetrazole, furan, pyrrole, isoxazole, imidazole, triazole and thiazole, including all positional isomers of said heterocyclic radicals;

$R_2$ represents a radical selected from the group consisting of hydrogen, hydroxy, thio, alkoxy, carboxy, carboxyalkyl, amino, alkylamino, dialkylamino, carboxamide, carboxamidoalkyl, sulfonamide acetamido;

X represents a valence bond or a divalent linking moiety selected from the group consisting of —N=CH—, —CH=N—, —(CH$_2$)$_n$—NH—, —NH—(CH$_2$)$_n$—, —(CH$_2$)$_n$—, —CH=CH— or —N=N—, n being an integer from 1 to 8;

Z represents a substituent selected from the group consisting of hydrogen, formyl, hydroxy or —X—Het, wherein X and Het are as previously defined; the isomeric forms of said compound and the pharmaceutically acceptable salts of said compound.

Particularly preferred are compounds having the formula:

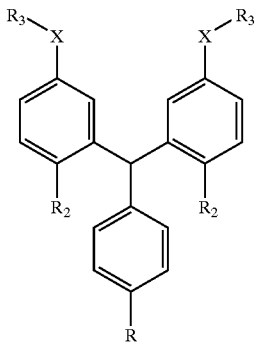

wherein X is a divalent linking moiety selected from the group of —N=C— or —CH=CH—; R is a radical selected from the group of hydrogen, hydroxy, alkoxy, alkyl, halogen, nitro or alkoxy monosubstituted with a substituent selected from carboxy, amino, monoalkylamino, dialkylamino or acetamido; R$_2$ is hydroxy; and R$_3$ is a heterocyclic radical selected from the group consisting of 1-pyrazolyl radicals, 1-triazolyl radicals (including the 1,2,3-;1,2,4-; or 1,3,4-isomers thereof), 4-triazolyl radicals, 1-tetrazolyl radicals or 2-tetrazolyl radicals (including the isomers thereof) and the amino- and alkyl-derivatives of such radicals, including, without limitation, 5-amino-1H-tetrazolyl, 3-amino-4H-1,2,4 triazolyl, 5-amino-1H-1,2,4 triazolyl, 5-amino-2H-tetrazolyl and 5-methyl-1H-tetrazolyl radicals.

In accordance with another aspect, the present invention provides a class of novel intermediates that are useful in preparing the anti-viral agents described herein. These intermediates have the general formula:

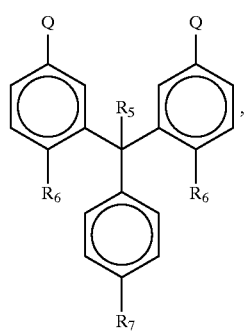

(II)

wherein Q represents a reactive group selected from those consisting of 5,5-dimethyl-1,3-dioxan and formyl; R$_5$ is a radical selected from those consisting of hydrogen and hydroxy; R$_6$ is a radical selected from those consisting of hydroxy, alkoxy, aryloxy and aralkoxy and R$_7$ is a radical selected from those consisting of hydrogen, hydroxy, alkoxy, alkoxyalkyl, halogen, perfluoroalkyl, thio, nitro, carboxy, carboxyalkyl, carbalkoxy, carbalkoxyalkyl, carboxamide, carboxamidoalkyl, alkyl, cycloalkyl, alkylthio, alkylsulfinyl, alkylsulfonyl, sulfonamide, amidino, cyano, amino, amido, alkylamino, dialkylamino, alkylaminoalkyl, or alkoxy monosubstituted with a substituent selected from the group consisting of carboxy, amino, alkylamino or dialkylamino.

The present invention also provides new synthetic methods for preparation of the compounds described herein. One method comprises causing a 3-halogen substituted-4-alkoxy-substituted benzaldehyde, in which the aldehyde moiety is protected with a protecting group, to undergo reaction with an alkylated alkali metal to effect a halogen-alkali metal exchange; adding to the reaction mixture an alkyl ester of an R-substituted benzoic acid under conditions yielding a dialkoxy-R-substituted triphenylcarbinol derivative including said protecting group; deprotecting and reducing the dialkoxy-R-substituted triphenylcarbinol derivative to restore the aldehyde functional groups and convert the triphenylcarbinol moiety to a triphenylmethane moiety; dealkylating any alkoxy substituents to hydroxy substituents; and reacting the aldehyde functional groups with an amine-substituted heterocyclic reactant to produce the desired product. The R substituents on the benzoic acid ester are selected from the group consisting of hydrogen, alkoxy, alkoxyalkyl, hydroxy, halogen, perfluoroalkyl, thio, nitro, carboxy, carboxyalkyl, carbalkoxy, carbalkoxyalkyl, carboxamide, carboxamidoalkyl, alkyl, cycloalkyl, alkylthio, alkylsulfinyl, alkylsulfonyl, sulfonamide, amidino, cyano, amino, amido, alkylamino, dialkylamino, alkylaminoalkyl, or alkoxy monosubstituted with a substituent selected from the group consisting of carboxy, amino, alkylamino or dialkylamino.

Another method for preparing compounds of this invention comprises reacting a 4,4'-dihydroxy-3,3'-(4-R-substituted phenyl)methylenebisbenzaldehyde, in which the hydroxy groups are etherified, with the anion of a methyl-substituted heterocyclic reactant to yield a heterocyclic hydroxyalkyl derivative of etherified, R-substituted triphenylmethane as an intermediate product; and subjecting the intermediate product to dehydration and deetherification to produce the desired product.

According to still another aspect, the present invention provides pharmaceutical compositions comprising one or more of the above-described compounds in combination with a pharmaceutically acceptable carrier medium.

In accordance with a further aspect, the present invention provides a method for preventing and treating pneumovirus infection and for preventing and treating diseases associated with pneumovirus infection in living hosts, by administering to a living host susceptible to pneumovirus infection a therapeutically effective amount of a compound of the above structures and/or the isomers and pharmaceutically acceptable salts of said compounds, or pharmaceutical compositions containing same.

DETAILED DESCRIPTION OF THE INVENTION

The compounds of the invention can be conveniently prepared from known starting materials according to one of the synthetic scheme illustrated below, wherein R and Het are as previously defined.

SCHEME A

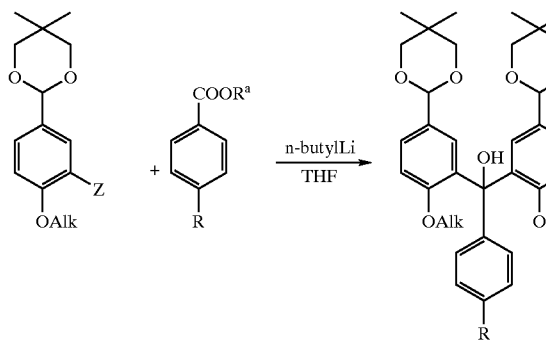

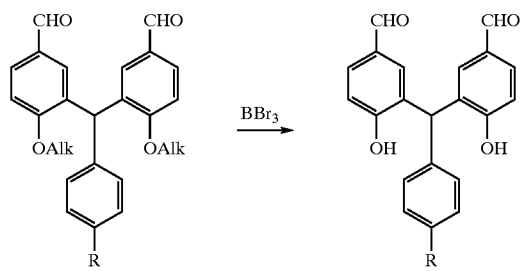

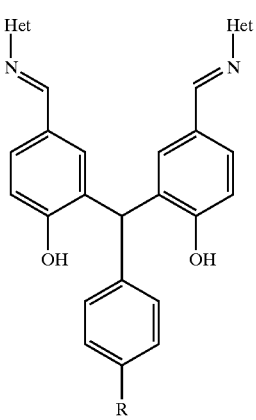

Alk=alkyl; Z=halogen, e.g., Br or 1; R$^a$=alkyl; R and Het previously defined

Synthetic scheme A involves protection of the aldehyde moiety of a bromobenzaldehyde followed by halogen-metal exchange and reaction of two equivalents of the desired aryl lithium species with an ester group to provide a triaryl methanol. Reduction and regeneration of the aldehyde can be achieved with formic acid. Liberation of the phenolic groups with boron tribromide (or pyridine hydrochloride) and condensation of the aldehyde groups with the appropriate heterocyclic amine provides the compounds of the invention.

SCHEME B

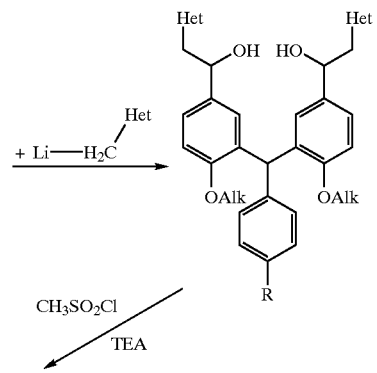

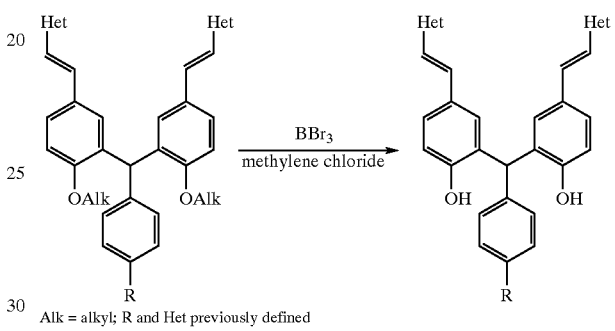

Alk = alkyl; R and Het previously defined

Synthetic scheme B involves the reaction of a bis aldehyde, prepared as described in Scheme A, above, with the anion of a methyl heterocycle generated from n-butyl lithium to give a heterocyclic hydroxyalkyl derivative of an etherified, R-substituted triphenylmethane, as an intermediate product. Dehydration of the intermediate with methane sulfonyl chloride provides the unsaturated compound which is deetherified with boron tribromide to give the desired compound.

The term "alkyl", as used herein, refers to aliphatic hydrocarbon radicals of one to six carbon atoms in length. Similarly, the term "alkyl", or any variation thereof, used in combination form to name substituents, such as alkoxy (—O-alkyl), alkylthio (—S-alkyl), alkylamino (—NH-alkyl), alkylsulfonyl (—S(O)$_2$-alkyl), carboxyalkyl (-alkyl-COOH), or the like, also refers to aliphatic hydrocarbon radicals of one to six carbon atoms in length, and preferably of one to four carbon atoms in length.

The designation "Het", as used herein, refers to an unsubstituted or substituted 5–7 membered heterocyclic ring substituent on the compounds of the invention, which substituent contains 1–3 heteroatoms selected from nitrogen, oxygen or sulfur, in which the heterocyclic ring substituent is at least one selected from the group of hydrogen, alkyl, amino, alkylamino or dialkylamino. Representative examples of such heterocyclic rings include, without limitation, those derived from pyrazole, triazole, tetrazole, oxadiazole, thiadiazole, imidazole, oxazole, thiazole, isoxazole, pyridine, pyrimidine, triazine, morpholine, piperidine, piperazine, 1,2,4-diazepine or the like.

The term "amido", as used herein, refers to a radical or substituent of the formula —NR"C(=O)R"', wherein R" and R"' represent hydrogen or alkyl.

The term "carboxamide", as used herein, refers to a radical or substituent of the formula —C(=O)—NR"R"', wherein R" and R"' are as previously defined.

The term "sulfonamide", as used herein, refers to a radical or substituent of the formula —SO$_2$NR"R'" or —NR"SO$_2$R'", wherein R" and R'" are as previously defined.

The term "carbalkoxy", as used herein, refers to a radical or substituent —C(=O)—OR", wherein R" is a previously defined.

Preparation of specific embodiments of anti-pneumovirus compounds within the scope of the invention are exemplified below.

In vitro studies have been performed demonstrating the usefulness of compounds described herein as antiviral agents against pneumoviruses. Antiviral activity was measured on the basis of activity against RSV in a cell culture assay.

All possible isomers of the compounds described herein are within the scope of the present invention. Representative examples of such isomers include, without limitation, cis and trans isomers.

The compounds described herein, their isomers and pharmaceutically acceptable salts exhibit antiviral activity against pneumoviruses and are within the scope of the present invention.

The compounds of the invention can form useful salts with inorganic and organic acids, including, for example, hydrochloric acid, hydrobromic acid, methanesulfonic acid salts, or the like, as well as with inorganic bases, such as sodium or potassium salts.

The pharmaceutically acceptable salts of the compounds of the invention are prepared following procedures which are familiar to those skilled in the art.

The antiviral pharmaceutical compositions of the present invention comprise one or more of the above-described compounds or precursors thereof, as the primary active ingredient in combination with a pharmaceutically acceptable carrier medium and, optionally one or more supplemental active agents.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the antiviral compounds of the invention, such as by producing any undesirable biological effect or otherwise interacting in a deleterious manner with any other component(s) of the pharmaceutical composition, its use is contemplated to be within the scope of this invention.

The compounds of the invention, any precursors thereof and their isomers and pharmaceutically acceptable salts are also useful in treating and preventing pneumovirus infections and diseases when used in combination with supplemental active agents, which may be optionally incorporated into the pharmaceutical composition of the invention, or otherwise administered during a course of therapy. These include, without limitation, interferons, ribavirin, and immunomodulators, immunoglobulins, anti-flammatory agents, antibiotics, anti-virals, anti-infectives, and the like, the combination of which with one or more compounds of the invention offers additive or synergistic therapeutic benefit.

In the pharmaceutical compositions of the invention, the active agent may be present in any therapeutically effective amount, which is typically at least 0.1% and generally not more than 90% by weight, based on the total weight of the composition, including carrier medium and/or supplemental active agent(s), if any. Preferably, the proportion of active agent varies between 1–50% by weight of the composition.

Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known carriers or excipients for medicaments may all be suitable as carrier media.

Compounds of the invention are usefull in treating and preventing pneumovirus infections (and diseases) in humans, as well as in livestock, and may be used to treat cattle, swine and sheep, or to treat avian species such as turkeys, or for other animals susceptible to pneumovirus infection. Thus, the term "patient" as used herein includes, without limitation, all of the foregoing.

Compounds described herein are also useful in preventing or resolving pneumoviral infections in cell cultures, tissue cultures and organ cultures, as well as other in vitro applications. For example, inclusion of compounds of the invention as a supplement in cell or tissue culture growth media and cell or tissue culture components will prevent pneunoviral infections of cultures not previously infected with pneumoviruses. Compounds described above may also be used to eliminate pneumoviruses from cultures or other materials infected or contaminated with pneumoviruses, after a suitable treatment period, under any number of treatment conditions as determined by the skilled artisan.

The compounds of the invention may be administered using any amount and any route of administration effective for attenuating infectivity of the pneumovirus. Thus, the expression "amount effective to attenuate infectivity of pneumovirus", as used herein, refers to a nontoxic but sufficient amount of the antiviral agent to provide the desired treatment of viral infection. The exact amount required will vary from subject to subject, depending on the species, age, and general condition of the subject, the severity of the infection, the particular antiviral agent and its mode of administration, and the like.

The anti-pneumovirus compounds are preferably formulated in dosage unit form for ease of administration and uniformity of dosage. Dosage unit form as used herein refers to a physically discrete unit of antiviral agent appropriate for the patient to be treated. Each dosage should contain the quantity of active material calculated to produce the desired therapeutic effect either as such, or in association with the selected pharmaceutical carrier medium. Typically, the antiviral compounds of the invention will be administered in dosage units containing from about 0.1 $\mu$g to about 50 mg of the antiviral agent, with a range of about 0.001 mg to about 25 mg being preferred.

The compounds of the invention, including their isomers and pharmaceutically acceptable salts, may be administered as such, or in the form of a precursor from which the active agent can be derived, such as a prodrug. A prodrug is a derivative of a compound described herein, the pharmacologic action of which results from the conversion by chemical or metabolic processes in vivo. Prodrugs of the compounds of the invention may include, but are not limited to mono-, di- or tri-esters of simple or functionalized aliphatic carboxylic acids; esters of carbamic acids ($R_a$—(O—CO—$NR_bR_c)_n$); esters of amino acids ($R_a$—(O—CO—CH(NH$_2$)$R_b)_n$); esters of unsubstituted or substituted aromatic acids ($R_a$—(O—CO—aryl)$_n$), wherein the aryl ring may be substituted with hydroxy, carboxy, lower alkyl, alkylthio, alkylsulphinyl, alkylsulphonyl, phosphoric acid, amino, alkylamido and halogen groups; esters of derivatized phosphoric acids; (acyloxy)methyl or acyloxy(ethyl)ethers ($R_a$—(O—CH$_2$—O—CO—$R_b)_n$ or $R_a$—(O—CH(CH$_3$)—O—CO—$R_b)_n$); (alkoxycarbonyloxy)methyl or (alkoxycarbonyloxy)ethyl ethers ($R_a$—(O—CH$_2$—O—CO—O—$R_b)_n$); and O-glycosides, wherein $R_a$ is a residue of a compound of the invention, $R_b$ and $R_c$ are aliphatic radicals ($C_1$–$C_{10}$) and n=1–3. Such prodrugs may be prepared according to procedures well known in the field of medicinal chemistry and pharmaceutical formulation science and are within the scope of the present invention.

The compounds of the invention may be administered orally, parenterally, such as by intramuscular injection, intraperitoneal injection, intravenous infusion or the like, or by inhalation, such as by aerosol, in the form of a solution or a dry powder, or the like, or by intubation, depending on the nature and severity of the infection being treated. The compounds of the invention may be administered orally, parenterally, or by inhalation or intubation at dosage levels of about $10^6$ mg to about 1000 mg/kg, one or more times a day, to obtain the desired therapeutic effect.

The compounds of the invention will typically be administered from 1 to 4 times a day so as to deliver the above-mentioned daily dosage. However, the exact regimen for administration of the compounds and compositions described herein will necessarily be dependent on the needs of the individual host being treated, the type of treatment administered and the judgment of the attending physician, veterinarian or medical specialist.

In view of the inhibitory effect on pneumovirus replication in cell culture produced by the compounds used in the method of the invention, it is anticipated that these compounds will be useful not only for therapeutic treatment of pneumovirus infection, but for pneumovirus prophylaxis, as well. The dosages will be essentially the same, whether for treatment or prophylaxis of pneumovirus infection.

The following examples are provided to describe the invention in further detail. These examples, which set forth the preferred mode presently contemplated for carrying out the invention, are intended to illustrate and not to limit the invention.

Examples 1–14 illustrate the chemical synthesis of representative compounds of the invention.

EXAMPLE 1

Preparation of 5,5'-Bis[1-(((5-amino-1H-tetrazolyl)imino)methyl)]2,2',4"-methylidynetrisphenol a. 2-(3-Bromo-4-methoxyphenyl)-5,5-dimethyl-1,3-dioxane. A solution of 3-bromo-4-methoxybenzaldehyde (74.65 g, 0.347 mol), neopentyl glycol (43.35 g, 0.416 mol), pyridinium p-toluenesulfonate (0.87 g, 0.035 mol), and benzene (1.8 L) was refluxed with azeotropic removal of water for 6 hours. The cooled reaction mixture was diluted with water. The aqueous phase was extracted with ethyl acetate. The combined organic phases were washed with brine, dried ($Na_2SO_4$), charcoaled, filtered through a short column of Florisil™, and concentrated in vacuo. There was obtained 102.8 g (98%) of ketal as a peach colored solid.

b. 5,5'-Bis(5,5 dimethyl-1,3-dioxan-2-yl)-2,2',4"trimethoxytriphenylmethanol. A solution of the dioxane derivative obtained in step a., above (150.6 g, 0.500 mol) in anhydrous THF (2.0 L) was cooled to −78° C. n-Butyllithium (50 mL of 10.0 M in hexanes) was added via syringe pump at about 1.0 mL/min. After 15 minutes, a solution of methyl 4-methoxybenzoate (33.24 g, 0.200 mol) in THF (350 mL) was added dropwise. The mixture was stirred at −78° C. for 15 minutes, at 0° C. for two and one-half hours, and quenched with 10% $NH_4Cl$ (1 L). t-Butyl methyl ether (1 L) was added and the layers separated. The aqueous phase was extracted with t-butyl methyl ether (two times, 1 L). The combined organic phases were washed with brine, dried ($MgSO_4$), filtered through Florisil™ and concentrated in vacuo. The yellow oil obtained was dissolved in methanol (1 L), seeded with a crystal of pure product, and chilled to 0° C. The resulting white solid was isolated, washed with cold methanol, and dried in vacuo to provide 102.8 g (88.8%) of the desired product.

c. 4,4'dimethoxy,-3,3'-(4-methoxyphenyl) methylenebisbenzaldehyde. The triarylcarbinol derivative (15.9 g, 0.0275 mol), produced as described in step b., above, was dissolved into formic acid (137 mL). The intense burgundy colored solution was heated at 100° C. for 13 hours, cooled to room temperature, and concentrated in vacuo. The white solid obtained was suspended in water, neutralized with saturated $NaHCO_3$, filtered, washed with water and hexane (removes neopentyl glycol bisformate) and dried in vacuo to provide 10.8 g (~100%) of nearly pure product as a faintly bluish powder.

d. 4,4'-dihydroxy-3,3'-(4-hydroxyphenyl) methylenebisbenzaldehyde. Boron tribromide solution (80 mL, 1M in methylene chloride) was added dropwise to a solution of the trimethyl ether (5.23 g, 0.0133 mol), resulting from the above-described deketalization, in dry methylene chloride. A mild exotherm to ~35° C. was observed during the addition. After 18 hr at room temperature, the reaction mixture was poured onto crushed ice (500 g) and stirred for 1 hour at room temperature. The resulting gray solid was extracted into ethyl acetate. The ethyl acetate solution was extracted three times with 10% $Na_2CO_3$. The combined aqueous extracts were treated with charcoal, filtered through Celite, and carefully acidified with 6N HCl. The off-white precipitate was isolated, washed with water, dried in vacuo, dissolved in THF (45 mL), diluted with t-butyl methyl ether (45 mL), and filtered through Florisil™ with THF/t-BME 1:1. Concentration of the filtrate provided 3.85 g (85%) of pure dialdehyde which contained a small amount of residual solvents.

e. Condensation with 1,5-Diaminotetrazole. A solution of the dialdehyde obtained from the above-described demethylation reaction (3.00 g, 8.61 mmol), dry N,N-dimethylformamide (120 mL), 1,5-diaminotetrazole (2.58 g, 25.8 mmol), and p-toluenesulfonic acid (0.33 g, 1.7 mmol) was stirred at 60° C. for 6 hours. The reaction mixture was cooled to room temperature and diluted with water (400 mL). The resulting off-white precipitate was isolated, washed with water, dissolved into tetrahydrofuran (150 mL), treated with charcoal, filtered, and concentrated in vacuo to provide 4.46 g of the title compound as a light yellow powder.

EXAMPLE 2

Preparation of 5,5'-Bis[1-(((5-amino-1H-tetrazolyl)imino)methyl)]-4"-methoxyphenyl-2,2'-benzylidenebisphenol a. 3-Bromo-4-hydroxybenzaldehyde. A mixture of 25.1 g (117 mmole) of 3-bromo4-methoxybenzaldehyde and 54.47 g (471 mmole) of pyridine hydrochloride was heated under nitrogen to 100° C. for 2 hours. After cooling to room temperature, the mixture was diluted with 1 liter of water and 500 ml of ethyl acetate. The organic layer was collected and the aqueous layer was extracted with three 500 ml portions of ethyl acetate and the combined organic layers were washed with water and dried. Removal of the solvent provided 22 g of an orange solid.

b. 4-Phenylmethoxy-3-bromobenzaldehyde. To a solution of 22 g (109 mmole) of 3-bromo-4-hydroxybenzaldehyde in 600 ml of acetone was added at room temperature under nitrogen 24.3 g (161 mmole) of milled potassium carbonate and 17.0 ml (143 mmole) of benzyl bromide and the mixture heated to reflux with stirring for 2 hours. The reaction was quenched with water and the volume was reduced to half in vacuo, and the mixture extracted three times with 200 ml portions of ethyl acetate. The combined organic layers were concentrated to dryness. The residual solid was redissolved in 500 ml of acetone and passed through a celite column. Water was added to the acetone solution. A yellow solid separated which was collected and dried to give 24.5 g of material.

c. 2-(3-Bromo-4-Phenylmethoxyphenyl)-5,5-dimethyl-1,3-dioxane. A solution of the 24.5 g (84.2 mmole) of the benzaldehyde from the immediately preceding step, 12.3 g (112 mmole) of neopentyl alcohol and 220 mg of p-toluenesulfonic acid in 350 ml of benzene was heated to reflux for 5 hours. A Dean Stark trap was used to collect the water which was generated during the reaction. The reaction was quenched with 1 ml of triethylamine and stirred for 12 hours at room temperature. The mixture was poured into 300 ml of water and the organic layer collected. The aqueous layer was extracted with three 100 ml portions of ethyl acetate. The combined organic layers were dried and the solvent removed to give a yellow solid which was purified by recrystallization from ethanol to give 19.2 g of an orange solid.

d. 5-5'-Bis(5,5-dimethyl-1,3-dioxan-2-yl)-4"-methoxy-2,2"-dilphenylmethoxytriphenylmethanol. To a solution of 1.9 g (5.04 mmole) of the material obtained from the immediately preceding step in 15 ml of distilled tetrahydrofuran, cooled to −100° C. was added dropwise under nitrogen, 2.3 ml of a 2.5 M solution of n-butyllithium in hexane. After the addition was complete,a solution of ethyl 4-methoxybenzoate, (2.5 mmole), was added and the solution was stirred for 1.5 hours at −78° C. and stirred for 12 additional hours at 0° C. and then quenched with water. After warming to room temperature, the volume was reduced to half by concentration in vacuo and then the mixture was diluted with 25 ml of water and 25 ml of ethyl acetate. The layers were separated and the aqueous layer extracted with three 25 ml portions of ethyl acetate. The combined organic layers were dried and concentrated to dryness. The residual solid was purified by column chromatography on silica by eluting with 80:20, hexane/ethyl acetate to give 60 mg of material.

e. 4,4'-Dihydroxy-3,3'(4-methoxyphenyl) methylenebisbenzaldehyde. The intermediate from the immediately preceding step, 50.4 mg (0.069 mmole) was dissolved in 3 ml of formic acid and the solution heated for four hours at 100° C., cooled to room temperature, and then water, 3 ml, was added and a white suspension appeared. The mixture was stirred overnight at room temperature. The mixture was partioned between water and ethyl acetate and after drying and removal of the ethyl acetate, the residual solid was purified by column chromatography on silica eluting with 40:60 hexane/ethyl acetate to give a white solid.

f. Condensation with 1,5-Diaminotetrazole. A solution of the dialdehyde obtained from the reaction described immediately above, 11.6 mg (0.032 mmole), dry N,N-dimethylformamide, 9.2 mg (0.0999 mmote) of 1,5-diaminotetrazole and 0.25 ml of a 0.025 M solution of p-toluenesulfonic acid was heated to 60° C. for 17 hours. The solvent was removed in vacuo and the residue was triturated with water to give a beige solid which was collected and dried to give 10 mg of the titled compound.

Furthermore, compounds of formula II, above, may be made with various heterocyclic radicals ($R_3$) by replacing the 1,5-diaminotetrazole with other heterocyclic reactants, as described in Examples 3–6, below.

EXAMPLE 3

Preparation of 5,5'-Bis[1-(((5-amino-1H-1,2,4 triazolyl)imino)methyl)]-2,2', 4"t-methylidyne trisphenol The title compound was synthesized essentially according to the basic procedure described in Example 1; however, 2,3-diamino-1,2,4 triazolyl was used instead of 1,5-diaminotetrazole.

EXAMPLE 4

Preparation of 5,5'-Bis[4-(((3-amino-4H-1,2,4-triazolyl)imino)methyl)]-2,2',4"-methylidyne trisphenol The title compound was prepared essentially according to the basic procedure described in Example 1, above; however, 3,4-diamino-1,2,4-triazole was used instead of 1,5-diaminotetrazole.

EXAMPLE 5

Preparation of 5,5'-Bis[2-(((5-amino-2H-tetrazolyl) imino)methyl)]-2,2',4"-methylidynetrisphenol The title compound was prepared essentially according to the synthetic procedure set out in Example 1; however, the 1,5-diaminotetrazole in Example 1 was replaced with 2,5-diaminotetrazole.

EXAMPLE 6

Preparation of 5,5'-Bis[1-(((5-methyl-1H-tetrazolyl) imino)methyl)]-2,2',4"-methylidynetrisphenol The title compound was synthesized essentially according to the basic procedure described in Example 1; however, 1-amino-5-methyltetrazole was used in place of 1,5-diaminotetrazole.

As described in the following example, compounds of formula I, above, in which the $R_1$ radical is other than hydroxyphenyl may be prepared by substitution of a suitable ester for the methyl 4-methoxybenzoate in step b of the reaction sequence of Example 1, above.

EXAMPLE 7

Preparation of 5,5'-Bis[1-(((5-amino-1H-tetrazolyl) imino)methyl)]-2,2'-benzylidenebisphenol The title compound was synthesized essentially according to the basic procedure described above in Example 1; however, 4,4'-dihydroxy-3,3'-benzylidenebisbenzaldehyde was substituted for 4,4'-dihydroxy-3,3'-(4-hydroxyphenyl)

methylenebis-benzaldehyde. This intermediate was obtained by using methylbenzoate in place of methyl 4-methoxybenzoate in step b. of Example 1, above.

Other examples of substituted esters which may be used to prepare additional compounds having the structure of formula I, above, include alkoxy, halo, perfluoroalkyl, alkoxycarbonyl, alkylaminocarbonyl, alkylthio, alkylsulfinyl, alkylsulfonyl, alkyl, alkoxyalkyl benzoates and esters of pyridine, thiophene, imidazole, furan, pyrole, oxazole, triazole, oxadiazole, thiadiazole, pyrazole, tetrazole, isoxazole, thiazole carboxylates.

EXAMPLE 8

Preparation of 5,5'-Bis[1-(((5-amino-1H-tetrazolyl) imino) methyl)]2,2'-methylidenebisphenol a. 4.4'-Dihydroxy-3,3'-methylenebisbenzaldehyde. To a solution of 5.0 g (21.9 mmole) of 2,2'-methylenebis(4-methylphenol) in 100 ml of methanol was added dropwise at −78° C. under nitrogen with stirring, 19.89 g (87.6 mmole) of 2,3-dichloro-5,6-dicyanobenzoquinone in 100 ml of methanol. After 2 hours, the solution was diluted with water and stirred for 30 minutes. The mixture was extracted with two 100 ml portions of ethyl acetate. The combined organic layers were washed with saturated sodium chloride solution and dried over magnesium sulfate. The mixture was filtered and the solution concentrated to dryness to give a brown solid. The material was dissolved in ethyl acetate and passed through a column containing Florisil™ which was washed with ethyl acetate. The fractions were collected and the solvent removed to give 22 g of a yellow solid.

b. Condensation with 1,5-Diaminotetrazole. The title compound was obtained according to step e. in Example 1, above.

EXAMPLE 9

Preparation of 5,5'-Bis[1-(2-(5-(1-methyl-1H-tetrazolyl))ethenyl)]-2,2',4"-methylidynetrisphenol a. α,α'-Bis[5-(1-methyl-1H-tetrazolyl)methyl]-4,4'-dimethoxy-3,3'-(4-methoxyphenyl) methylenebisbenzenemethanol.

To a solution of 294 g (3.0 mmol) of 1,5-dimethyl-1H-tetrazole in freshly distilled tetrahydrofuran chilled to −78° C. was added dropwise over a 5 minute period 1.8 ml of a 1.7M solution of t-butyl lithium in pentane. The solution was stirred for 50 minutes and to the yellow suspension was added 390 mg (1.0 mmoles) of 4,4'-dimethoxy-3,3'-(4 methoxyphenyl) methylenebisbenzaldehyde in 15 ml of dry tetrahydrofuran over a 5 minute period. To the reaction mixture was added 10 ml of a 10% ammonium chloride solution. The mixture was warmed to room temperature and partitioned between water (25 ml) and ethyl acetate (25 ml). The aqueous layer was collected and extracted with 25 ml of ethyl acetate. The combined organic layers were washed with a saturated sodium chloride solution and dried. Removal of the solvent gave 346 mg of a pale yellow solid.

b. 5,5'-Bis[1-(2-(5-(1-methyl-1H-tetrazolyly)ethenyl)]-2,2',4'-trimethoxytriphenylmethane.

A solution of 346 mg (0.592 mmoles) of the material from step a, above, 0.28 ml of triethylamine, 12 mg (0.1 mmol) of 4-dimethylaminopyridine (DMAP) in 5 ml of dry methylene chloride was chilled in an ice bath. To the solution was added 0.15 ml (2.0 mmole) of methanesulfonyl chloride and the solution stirred for 2 hours in an ice bath and then allowed to slowly warm to room temperature and left for 16 hours. To the solution was added 10 ml of ethyl acetate and the solution washed with two 10 ml portions of water, 1 N hydrochloric acid and a saturated solution of sodium chloride, and then dried over magnesium sulfate. Removal of the solvent gave 348 mg of a solid which was dissolved in 5 ml of tetrahydrofuran. To this solution was added 90 mg of 1,8-diazobicyclo[5.4.0]-undec-7-ene. An oily material appeared and the mixture stirred for 16 hours. The mixture was diluted with 15 ml of ethyl acetate and extracted with 15 ml of water. The organic layer was collected, washed with water and dried. Removal of the solvent resulted in 348 g of the desired product.

c. Demethylation with Boron Tribromide

To a suspension of 110 mg (0.2 mmole) of the material prepared in step b., above, dissolved in 1 ml of dry methylene chloride, cooled to 0° C. was added 1.2 ml of 1.0 M boron tribromide in methylene chloride. The mixture was stirred for 2 hours and the yellow solid which formed was collected, washed with water and suspended in 15 ml of water. To the suspension was added 5% sodium hydroxide until a solution was obtained. The solution was treated with charcoal and the suspension filtered through Celite 503 and the solution acidified with 1 N hydrochloric acid. The resulting white solid was collected by filtration, washed with water and dried to give 73 mg of product.

EXAMPLE 10

Preparation of 5,5'-Bis[((1-(5-methyl-1H-tetrazolyl) imino)methyl)]-(4-propylphenyl)-2,2'-benzylidinebisphenol a. 5,5'-Bis(5,5-dimethyl-1,3-dioxan-2-yl-2,2'-dimethoxy-4"-propyltriphenylmethanol.

To a solution of 15.0 g (49.8 mmole) of 2-(3-bromo-4-methoxyphenyl)-5,5-dimethyl-1,3-dioxane in 120 ml of dry THF at −78° C. was added dropwise 24 ml of 2.5 M n-butyllithium. After the addition was complete, 3.82 g (59.7 mmole) of ethyl 4-propyl benzoate in 30 ml of THF was added dropwise and after the addition was complete, the mixture was allowed to warm to room temperature and stirred for 12 hours. One hundred ml of saturated ammonium chloride was added followed by 100 ml of i-butyl methyl ether. The organic layer was separated and washed with water, dried and the solvent removed to give 6.41 g of crude material. This was passed through silica and eluted with 50% ethyl acetate-50% hexane, and the solvents removed to give 4.92 g of product.

b. 4,4'-Dimethoxy-3,3'-(4-propylphenyl)methylene bis-benzaldehyde

A solution of 4.3 g (7.28 mmole) of the material prepared in step a., above, in 30 ml of formic acid was heated to reflux for 4 hours. After cooling, water (100 ml) was added and the mixture extracted with two 100 ml portions of methyl t-butylether. The combined organic extracts were washed with water, dried and the solvent removed. The residual solid was passed through silica gel and eluted with 50% ethyl acetate-50% hexane to give, after removal of the solvent, 1.98 g of the desired solid.

c. 4,4'-Dihydroxy-3,3'-(4-propylphenyl) methylenebisbenzaldehyde.

To a solution of 1.1 g (2.73 mmole) of the methyl ether from step b., above, in 15 ml of methylene chloride was added at room temperature 10.9 ml (10.9 mmole) of boron tribromide over a 5 minute period and then stirred at room temperature for 12 hours. The reaction mixture was poured into ice water and the organic layer separated and dried. Removal of the solvent gave 750 mg of a greenish-brown solid.

d. Condensation with 1-amino-5-methyltetrazole

This reaction was run in the same fashion as previously described.

EXAMPLE 11

Preparation of 5,5'-Bis[((1-(5-methyl-1H-tetrazolyl)imino)methyl)]-(4'-propyloxyphenyl)-2,2'-benzylidenebisphenol a. 4,4'-Diallyloxy-3,3'-(4-propyloxyyhenyl)methylenebisbenzaldehyde.

To a solution of 5.0 g (11.8 mmole) of 4,4'-Diallyloxy-3,3'(4-hydroxyphenyl)methylenebisbenzaldehyde and 3.26 g (23.6 mmole) of potassium carbonate in 40 ml of N-methylpyrrolidone was added 2.3 ml (23.6 mmole) of n-propyliodide. The mixture was warmed to 90° C. for 3 hours after which time an additional 5 ml of n-propyliodide was added. The reaction was heated for an additional 12 hours after which time it was diluted with 100 ml of water and extracted 3 times with 50 ml. of t-butyl methyl ether. The combined organic extracts were washed with water and dried to give 6.86 g of a crude product which was passed through a silica gel column and eluted with 50% ethyl acetate and 50% hexane. After removal of the solvent, 4.43 g of yellow solid was obtained.

b. 4,4'-Dihydroxy-3,3'-(4-propyloxyphenyl)methylenebisbenzaldehyde.

Ruthenium trichloride, 230 mg (0.89 mmole) was added to a refluxing solution of 4.12 g (8.95 mmole) of the diallyl protected ether, prepared in step a., above, in 120 ml of ethanol. After 90 minutes, an additional 100 mg of ruthenium trichloride was added. After 6 hours, the solvent was removed and the residue dissolved in ethyl acetate and passed through silica gel and eluted with 60% ethyl acetate-40% hexane. After removal of the solvent, 2.95 g of a brown solid was obtained which was redissolved and again passed through a silica gel column to give 1.73 g of product.

c. Condensation with 1-amino-5-methyltetrazole.

This reaction was run as previously described in example 6.

EXAMPLE 12

Preparation of 5,5'-Bis[((1-(5-methyl-1H-tetrazolyl)imino) methyl)]-(4-fluorophenyl)-2,2'-benzylidenebisphenol a. 5,5-Bis(5,5'-dimethyl-1,3-dioxan-3-yl)-2,2'-dimethoxy-4"-fluorotriphenylphenylmethanol.

The reaction was run as previously described using 2-(3-Bromo-4-methoxyphenyl)-5,5'-dimethyl-1,3-dioxane and methyl 4-fluorobenzoate.

b. 4,4'-Dihydroxy-3,3'-(4-fluorophenyl)methylenebisbenzaldehyde.

This compound was prepared as previously described from the compound prepared in step a., above, and formic acid, followed by boron tribromide demethylation.

c. Condensation with 1-amino-5-methyltetrazole.

This reaction was run as previously described.

EXAMPLE 13

5,5'-Bis[1-(2-(4-methylthiazolyl)ethenyl)]-2,2',4"-methylidynetrisphenol a. 4,4'-Dibenzyloxy-3,3'-(4-benzyloxyphenyl)methylenebisbenzaldehyde.

To a solution of 2.0 g (5.74 mmole) of 4,4'-dihydroxy-3,3'-(4-hydroxyphenyl)methylenebisbenzaldehyde in 57 ml of DMF was added 7.95 g (5.76 mmole) of potassium carbonate and 4.09 g (23.9 mmole) of benzylbromide. The mixture was stirred for 12 hours at room temperature and then heated to reflux for 2 hours. The reaction mixture was diluted with water (100 ml) and then extracted with ethyl acetate. The organic extracts were combined, dried and the solvent removed . The residue was purified by HPLC by eluting with 60-40 ethyl acetate-hexane to give 3.25 g of product b. α,α'-Bis[2-(4-methylthiazolyl)methyl]-4,4'-dibenzaloxy-3,3'-(4-benzyloxyphenyl)methylenebisbenzenemethanol.

A solution of 2.4 ml (21.3 mmole) of 2,4-dimethylthiazole in 48 ml of dry THF was cooled to −78° C. and to the solution was added dropwise 11.64 ml of a 2.5 M solution of n-butyllithium in hexanes. After stirring for 1 hour, 6.0 g (9.7 mmole) of the aldehyde prepared in step a., above, in 20 ml of THF was added dropwise. The reaction mixture was stirred for an additional 2 hours and then allowed to come to room temperature and stirred for an additional 12 hours. The mixture was diluted with 60 ml of saturated ammonium chloride solution and the THF was removed by concentration of the mixture in vacuuo. The residue was extracted 3 times with ethyl acetate and the combined organic layers were dried and concentrated to dryness to give 8.72 g of crude material which was purified by HPLC, eluting with 70–30 hexane-ethyl acetate providing 2.49 g of product.

c. 5,5'-Bis[1-(2-(2-(4-methylthiazolyl))ethenyl)]-2,2',4"-tribenzyloxy triphenylmethane.

A solution of 500 mg (0.592 mmole) of the alcohol from step b., above, in 16 ml of acetic anhydride was heated to reflux for 5 hours. After cooling, the solution was diluted with water and extracted three times with ethyl acetate. The combined extracts were washed with water, dried and the solvent removed. The crude product was purified by HPLC, eluting with 70–30 hexane-ethyl acetate to give 390 mg of product.

d. 55 '-Bis[1-(2-(4-methylthiazolyl)ethenyl]-2,2',4"-methylidinetrisphenol.

A solution of 570 mg (0.705 mmole) of the material prepared in step c., above, in 46 ml of formic acid was heated to reflux for 12 hours. The cooled solution was diluted with water and extracted three times with ethyl acetate. The combined organic extracts were washed with water, dried and the solvent evaporated to dryness. The crude material was purified by recrystallization from methylene chloride.

EXAMPLE 14

Preparation of 5,5'-Bis[1-(2-(5(3-methylisoxazolyl))ethenyl)]-phenyl-2,2'-benzylidenebisphenol a. α,α'-Bis[5-(3-methylisoxazolyl)methyl]-4,4'-dimethoxy-3,3'-(phenyl)methylenebisbenzaldehyde.

A solution of 2.9 ml (3.0 mmole) of 3,5-dimethylisoxazole in 150 ml of dry THF was cooled to −80° C. To this solution was added 12 ml of 2.5 M n-butyllithium in hexanes. After the addition was complete, 3.6 g (1.0 mmole) of 4,4'-dimethoxy-3,3'-(phenyl)methylenebisbenzaldehyde was added over 1 hour After the addition was complete, a saturated ammonium chloride solution was added. The mixture was partitioned between water and methyl t-butylether. The organic layer was collected, dried and the solvent removed to give 5.59 g of product.

b. This reaction was performed in the same general manner as described in Example 9, step b.

c. Demethylation.

A mixture of 260 mg (0.5 mmole) of the compound obtained in step b., above, and 3.5 g of pyridine hydrochloride were heated to 220° C. for 6 hours. The mixture was diluted with water and a solid separated. The solid was dissolved in ethyl acetate and the solution extracted with water, treated with charcoal, filtered and the solvent removed to give , after drying, 128 mg of the desired product.

Other compounds of the invention having anti-pneumovirus activity may be prepared following the various synthetic routes described hereinabove. Additional examples include, without limitation, 5,5'-Bis[2-(2-(5-methyl-2H-tetrazolyl)ethyl)]-2,2',4"-methylidynetrisphenol; 5,5'-bis[((1-(5-methyl-1H-tetrazolyl)amino)methyl)]-2,2', 4"-methylidynetrisphenol; 5-[((1-(5-methyl-1H-tetrazolyl) imino)methyl)]-2,2',4"-methylidynetrisphenol; 5-[((1-(5-methyl-1H-tetrazolyl)imino)methyl)]-2,4',4"-methylidynetrisphenol; 3-[5-[((1-(5-methyl-1H-tetrazolyl) imino)methyl)]-2,4'-dihydroxydiphenylmethylene]-4-hydroxybenzaldehyde; 5,5'-bis[((1-(5-methyl-1H-tetrazolyl)imino)methyl)]-[4-((2-diethylamino)ethoxy) phenyl]-2,2'-benzylidenebisphenol; 4-[5,5'-bis[((1-(5-methyl-1H-tetrazolyl)imino)methyl)]-2,2'-dihydroxydiphenylmethylene]phenoxyacetic acid; 5,5'-bis [((1-(5-methyl-1H-tetrazolyl)imino)methyl)]-(4-pyridinyl)-2,2'-benzylidenebisophenol; 5,5'-bis[((1-(5-methyl-1H-tetrazolyl)imino)methyl)]-(4-nitrophenyl)-2,2'-benzylidenebisphenol; 5,5'-bis[((1-(5-methyl-1H-tetrazolyl) imino)methyl)]-(4-nitrophenyl)-2,2'-benzylidenenbisphenol; 5,5'-bis[1-(2-(2-(1-methylimidazolyl))ethenyl)]-2,2',4"-methylidynetrisphenol; and 5,5'-Bis[1-(((5-methyl-1H-tetrazolyl)imino)methyl)] phenyl-2,2'-benzylidenebisphenol.

Illustrative examples of the preparation of prodrugs in accordance with the present invention are provided below.

EXAMPLE 15

Preparation of Prodrugs a) A solution of 255 mg (0.5 mmoles) of the compound prepared as described in Example 1, above, in 2.5 ml of anhydrous pyridine and 0.243 ml of acetic anhydride was left at room temperature overnight. The solvent was removed and to the residue was added 5 ml of water and the mixture was made slightly acidic by the addition of acetic acid. The solid was collected, washed with water followed by hexane and then dried to give 240 mg of the desired triacetate prodrug.

b) Following essentially the same procedure, 220 mg of the triacetate derivative was obtained from 200 mg of the compound prepared as described in Example 6, above.

Example 16 illustrates the effectiveness of the compounds used in the method of the invention in inhibiting the viral replication of RSV in cell culture.

EXAMPLE 16

Cell Culture Assay for Inhibition of Pneumovirus Replication

The replication of many viruses may be quantitatively assessed in the laboratory in various cell or tissue culture systems. Such in vitro culture methodologies are available and useable by those skilled in the art for the propagation and quantitative measurement of the replication of pneumoviruses. The following procedure was used for the in vitro quantitative measure of RSV replication.

Using the procedure described in this example, compounds of the present invention were evaluated for their ability to inhibit the replication of the virus in cell culture. By adding compounds at various concentrations to the culture medium, a dose response effect of the compound on virus replication was determined. A useful quantitative measure of the inhibition of RSV replication in this assay is the concentration of the compound at which virus replication in cell culture is inhibited by 50% in comparison to that observed in the absence of the compound (50% Inhibitory Concentration, $IC_{50}$). In the case of RSV, $IC_{50}$ values are defined as the concentration of compound that protected 50% of the cell monolayer. from virus-induced cytopathic effect (syncytia formation).

Anti-pneumovirus compounds of the invention were screened for antiviral activity against RSV (strain Long) on cultured HEp2 cells. Standard 96-well culture plates were seeded with $4 \times 10^4$ HEp2 cells in 200 µL of Minimal Essential Medium with Earles salts (EMEM) supplemented with 10% fetal bovine serum (FBS). Twenty-four to 30 hours later, the cells were infected with a dilution of RSV in Medium 199 (GIBCO/BRL) with 5% FBS that had been titrated to yield>85% destruction of the cell monolayer in 60 hours. After 1 hour at 370° C., compounds were added to wells of the plate in a final DMSO concentration of 0.5% as a series of 10 two-fold dilutions of the compound. Virus control wells (VC, no test compound) and cell culture control wells (CC, no virus, no test compound) were also included on each plate. Plates were incubated in a humidified atmosphere at 37° C. and 5% carbon dioxide. After 60 hours, 100 µL of a 5% solution of glutaraldehyde in water was added to each well, and the wells were incubated at room temperature for 1 hour. The fixative was removed, and the cells were stained with a 0.1% solution of crystal violet in water for 15–30 minutes. After rinsing and drying the plates, the optical density of the wells was measured at 570 nm ($OD_{570}$).

To determine $IC_{50}$ values for the test compounds, the mean value of the $OD_{570}$ readings of the virus control wells (VC) on a plate was substracted from the $OD_{570}$ readings of all wells on that plate. The $IC_{50}$ values were then calculated according to the following formula:

$$IC_{50}=[(Y-B)/(A-B)]\times(H-L)+L$$

where Y represents the mean $OD_{570}$ reading of the cell control wells (CC) divided by 2; B represents the mean $OD_{570}$ reading of wells of the compound dilution nearest to and below Y; A represents the mean $OD_{570}$ reading of wells of the compound dilution nearest to and above Y; L represents the compound concentration at B; and H represents the compound concentration at A.

A similar assay is useful for various strains of human RSV, including subtype A and subtype B viruses, as well as other pneumoviruses.

The results of the cell culture assay for inhibition of the replication of several pneumoviruses for representative compounds used in the method of the invention are given in Table 1.

TABLE 1[1]

| Example | RSV-A | RSV-B | BRSV | ORSV | GRSV |
|---|---|---|---|---|---|
| 1 | 0.001 | 0.008 | 0.003 | 0.002 | 0.001 |
| 2 | 0.001 | 0.008 | 0.001 | n.d. | n.d. |
| 3 | 0.050 | 0.46 | 0.010 | 0.17 | n.d. |
| 4 | 0.110 | 0.15 | 0.270 | n.d. | n.d. |
| 5 | 0.090 | 1.9 | 1.7 | 1.2 | n.d. |
| 6 | 0.001 | 0.002 | 0.001 | 0.001 | 0.001 |
| 7 | 0.001 | n.d. | n.d. | n.d. | n.d. |
| 8 | 0.370 | 47.3 | 16.2 | n.d. | n.d. |
| Ribavirin | 24.3 | 17.7 | 7.5 | 15.5 | 3.3 |

[1]All data represent $IC_{50}$ values in $\mu$M; abbreviations; RSV-A = human RSV subtype A; human RSV-B = RSV subtype B; BRSV = bovine RSV; ORSV = ovine RSV; GRSV = goat RSV; n.d. = not done.

The low concentrations of test compounds required to achieve 50% inhibition of RSV replication in cell culture indicate that the compounds used in the method of the invention are effective at inhibiting the pneumovirus replication process. It is also demonstrated here that the compounds of the invention are dramatically more potent than Ribavirin at inhibiting viral replication.

Example 17 demonstrates that the compounds of the invention are not toxic or detrimental to the health of normal cells at concentrations well above those needed to inhibit pneumovirus replication.

EXAMPLE 17

Assay for Cytotoxicity of Inhibitors of Pneumovirus Replication

To demonstrate that the compounds of the invention are not toxic or detrimental to the health of normal cells, compounds of the invention were evaluated in an in vitro cytotoxicity assay. One usefull assay for determining the cytotoxic effects of compounds on the growth of cells is a tetrazolium-based calorimetric method (Mossman, T., J. Immun. Methods, 65 (1–2): 55–63 (1983)). This assay measures cell viability, and therefore cytotoxicity, by quantitatively detecting the in situ reduction of 3-(4,5-dimethylthiazol-2-yl)-2,5-diphenyltetrazolium bromide (MTT) by viable cells. Cells are seeded in 96-well plates in DMEM containing 5% FBS at a density of $4\times10^3$ cells per well. After incubation for 4 hours at 37° C. and 5% $CO_2$, 2-fold serial dilutions of compound in 1% DMSO (or solvent alone) are added to quadruplicate wells and the plates are incubated for an additional 68 hours at 37° C. and 5% $CO_2$, which is equivalent to 3 to 4 cell doublings. The culture medium is removed, and the cells are treated with 1 mg/ml of MTT in phosphate-buffered saline, pH 7.2 for 4 hours at 37° C. and 5% $CO_2$. After removal of the unreduced MTT, the reduced blue formazan crystals produced by the viable cells are solubilized by the addition of 0.04N HCl in isopropanol. The optical density at 570 nm ($OD_{570}$) of each well is read using a suitable microplate reader. Cell viability is expressed as the percentage of optical density for compound-treated cells relative to the optical density of solvent alone-treated control wells. The highest compound concentration resulting in an optical density of$\geqq$75% of the control is represented as the cellular cytotoxicity value ($CC_{75}$).

The results of the MTT cytotoxicity assay using compounds prepared according to Examples 1 through 8 are given in Table 2.

TABLE 2

| Example | $CC_{75}$ ($\mu$M) | $IC_{50}$ ($\mu$M)[1] | SI |
|---|---|---|---|
| 1 | >12.5 | 0.001 | >12,500 |
| 2 | >150 | 0.001 | >150,000 |
| 3 | 12.5 | 0.05 | 250 |
| 4 | 18.8 | 0.11[2] | 171 |
| 5 | >50.0 | 0.09[2] | >556 |
| 6 | 3.1 | 0.001 | 3,100 |
| 7 | >6.3 | 0.001 | >6,250 |
| 8 | 9.4 | 0.37[2] | 25 |
| Ribavirin | 9.4 | 24.3 | <1 |

[1]Activity against human RSV subtype A.
[2]Protection from viral cytopathic effect of cell cultures achieved only 70–90% at highest compound concentrations tested.

As shown in Table 2, the cellular cytotoxicity ($CC_{75}$) values for the compounds of Examples 1 through 8 are considerably higher than the antiviral ($IC_{50}$) values for these compounds. These results indicate that the compounds of the invention are highly selective and, at therapeutically effective doses, they do not detrimentally affect the health of normal cells. A measure of this selectivity is provided by the high selective index value (SI), which is defined as $CC_{75}/IC_{50}$. The high SI values exhibited by compounds of the invention indicate very desirable attributes of the compounds.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound having the formula:

(I)

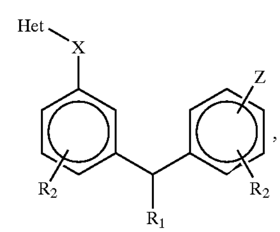

, wherein Het represents an unsubstituted or substituted five to seven membered heterocyclic ring containing one to three heteroatoms selected from nitrogen, oxygen or sulfur, said heterocyclic ring substituents being at least one selected from those consisting of alkyl, amino, monoalkylamino or dialkylamino;

R1 represents a radical selected from the group consisting of halogen; perfluoroalkyl; alkoxyalkyl; amino; alkylamino; dialkylamino; amido; alkylaminoalkyl; an unsubstituted or substituted, saturated or unsaturated straight- or branched-chain alkyl radical, said alkyl chain substituent being at least one hydroxy group; carboxy; an unsubstituted or substituted phenyl radical ($C_6H_5$), said phenyl radical substituent being at least one selected from the group consisting of hydroxy, halogen, perfluoroalkyl, thio, nitro, carboxy, carboxyalkyl, carbalkoxy, carbalkoxyalkyl, carboxamide, carboamidoalkyl, alkyl, cycloalkyl, alkoxy, alkoxyalkyl, alkylthio, alkylsulfinyl, alkylsulfonyl, sulfonamide, amidino, cyano, amino, amido, alkylamino, dialkylamino, alkylaminoalkyl, or alkoxy monosubstituted with a substituent selected from the group consisting of carboxy, amino, alkylamino or dialkylamino; a cycloalkyl radical; or a heterocyclic radical selected from the group consisting of pyridine, thiophene, oxazole, oxadiazole, thiadiazole, pyrazole, tetrazole, furan, pyrrole, isoxazole, imidazole, triazole and thiazole, including all positional isomers of said heterocyclic radicals;

R2 represents a radical selected from the group consisting of hydrogen, hydroxy, thio, alkoxy, carboxy, carboxyalkyl, amino, alkylamino, dialkylamino, carboxamide, carboxamidoalkyl, or sulfonamide;

X represents a divalent linking moiety selected from the group consisting of —N=CH—, —CH=N—, —(CH$_2$)$_n$—NH—, —NH—(CH$_2$)$_n$—, —(CH$_2$)$_n$—, —CH=CH— or —N=N—, n being an integer from 1 to 8;

Z represents a substituent selected from the group consisting of formyl, hydroxy or —X—Het, wherein X and Het are as previously defined; the isomeric forms of said compound and the pharmaceutically acceptable salts of said compound.

2. The compound 5,5'-Bis[1-(((5-amino-1H-tetrazolyl)imino)methyl)]2,2',4"-methylidynetrisphenol as claimed in claim 1.

3. The compound 5,5'-Bis[1-(((5-amino-1H-tetrazolyl)imino)methyl)]-4"-methoxyphenyl-2,2'-benzylidenebisphenol as claimed in claim 1.

4. The compound 5,5'-Bis[1-(((5-amino-1H-1,2,4 triazolyl)imino)methyl)]-2,2',4"-methylidynetrisphenol as claimed in claim 1.

5. The compound 5,5'-Bis[4-(((3-amino-4H-1,2,4-triazolyl)imino)methyl)]-2,2',4"-methylidynetrisphenol as claimed in claim 1.

6. The compound 5,5'-Bis[2-(((5-amino-2H-tetrazolyl)imino)methyl)]-2,2',4"-methylidynetrisphenol as claimed in claim 1.

7. The compound 5,5'-Bis[1-(((5-methyl-1H-tetrazolyl)imino)methyl)]-2,2',4"-methylidynetrisphenol as claimed in claim 1.

8. The compound 5,5'-Bis[1-(((5-amino-1H-tetrazolyl)imino)methyl)]-2,2'-benzylidenebisphenol as claimed in claim 1.

9. The compound 5,5'-Bis[1-(((5-amino-1H-tetrazolyl)imino)methyl)]2,2'-methylidenebisphenol as claimed in claim 1.

10. The compound 5,5'-Bis[1-(2-(5-(1-methyl-1H-tetrazolyl))ethenyl)]-2,4',4"-methylidynetrisphenol as claimed in claim 1.

11. The compound 5,5'-Bis[((1-(5-methyl-1H-tetrazolylimino)methyl)]-(4-propylphenyl)-2,2'-benzylidinebisphenol as claimed in claim 1.

12. The compound 5,5'-Bis[((1-(5-methyl-1H-tetrazolyl)imino)methyl)]-(4-propyloxyphenyl)-2,2'-benzylidenebisophenol as claimed in claim 1.

13. The compound 5,5'-Bis[((1-(5-methyl-1H-tetrazolyl)imino)methyl)]-(4-fluorophenyl)-2,2'-benzylidenebisphenol as claimed in claim 1.

14. The compound 5,5'-Bis[1-(2-(4-methylthiazolyl)ethenyl)]-2,2',4"-methylidynetrisphenol as claimed in claim 1.

15. The compound 5,5'-Bis[1-(2-(5-(3-methylisoxazolyl))ethenyl)]-phenyl-2,2'-benzylidenebisphenol as claimed in claim 1.

16. The compound 5,5'-Bis[2-(2-(5-methyl-2H-tetrazolyl)ethyl)]-2,2',4"-methylidynetrisphenol as claimed in claim 1.

17. The compound 5,5'-Bis[((1-(5-methyl-1H-tetrazolyl)amino)methyl)]-2,2',4"-methylidynetrisphenol as claimed in claim 1.

18. The compound 5-[((1-(5-methyl-1H-tetrazolyl)imino)methyl)]-2,2',4"-methylidynetrisphenol as claimed in claim 1.

19. The compound 5-[((1-(5-methyl-1H-tetrazolyl)imino)methyl)]-2,4',4"-methylidynetrisphenol as claimed in claim 1.

20. The compound 3-[5-[((1-(5-methyl-1H-tetrazolyl)imino)methyl)]-2,2'-dihydroxydiphenylmethylene]-4-hydroxybenzaldehyde as claimed in claim 1.

21. The compound 5,5'-Bis[((1-(5-methyl-1H-tetrazolyl)imino)methyl)]-[4-((2-diethylamino)ethoxy)phenyl]-2,2'-benzylidenebisphenol as claimed in claim 1.

22. The compound 4-[5,5'-Bis[((1-(5-methyl-1H-tetrazolyl)imino)methyl)]-2,2'-dihydroxydiphenylmethylene]phenoxyacetic acid as claimed in claim 1.

23. The compound 5,5'-Bis[((1-(5-methyl-1H-tetrazolyl)imino)methyl)]-(4-pyridinyl)-2,2'-benzylidenebisphenol as claimed in claim 1.

24. The compound 5,5'-Bis[((1-(5-methyl-1H-tetrazolyl)imino)methyl)]-(4-nitrophenyl)-2,2'-benzylidenebisphenol as claimed in claim 1.

25. The compound 5,5'-Bis[((1-(5-methyl-1H-tetrazolyl)imino)methyl)]-(4-aminophenyl)-2,2'-benzylidenebisphenol as claimed in claim 1.

26. The compound 5,5'-Bis[1-(2-(2-(1-methylimidazolyl)ethenyl)]-2,2',4"-methylidynetrisphenol as claimed in claim 1.

27. The compound 5,5'-Bis[1-(((5-methyl-1H-tetrazolyl)imino)methyl)]phenyl-2,2'-benzylidenebisphenol as claimed in claim 1.

28. A pharmaceutical composition for treating or preventing pneumovirus infection, said composition comprising a compound as claimed in claim 1 in an amount effective to attenuate infectivity of said virus, and a pharmaceutically acceptable carrier medium.

29. A pharmaceutical composition as claimed in claim 1, further comprising at least one supplemental active agent selected from the group consisting of interferons, ribavirin and immunomodulators, immunoglobulins, anti-flammatory agents, antibiotics, anti-virals and anti-infectives.

30. A method of treatment of pneumovirus infection in a patient in need of said treatment, said method comprising administering to said patient a therapeutically effective amount of a compound as claimed in claim 1 or a precursor of said compound.

31. A method of preventing pneumovirus infection in a host susceptible to said infection, said method comprising administering to said host a prophylactically effective amount of a compound as claimed in claim 1, or a precursor of said compound.

32. A method of treating cells in culture that are susceptible to infection by, or infected or contaminated with a pneumovirus, said method comprising administering to said cultures an effective amount of a compound as claimed in claim 1.

33. A compound having the formula

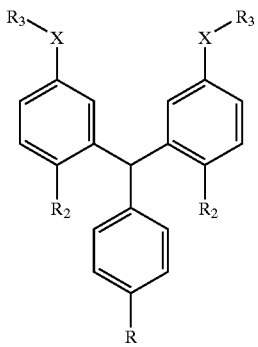

wherein X is a divalent linking moiety selected from the group of —CH=CH—, or —N=C—, the nitrogen of said divalent linking moiety being bound to $R_3$ R is a radical selected from the group of hydrogen, hydroxy, alkoxy, alkyl, halogen, nitro or alkoxy monosubstituted with a substituent selected from carboxyl, amino, monoalkylanino, dialkylamino or acetamido; $R_2$ is hydroxy; and $R_3$ is an unsubstituted heterocyclic radical selected from the group consisting of a 1-pyrazolyl radical, a 1-triazolyl radical, a 4-triazolyl radical, 1-tetrazolyl radical, or a 2-tetrazolyl radical, or a substituted heterocyclic radical selected from the group consisting of 5-amino-1H-tetrazolyl, 3-amino-4H-1,2,4 triazolyl, 5-amino-1H-1,2,4 triazolyl, 5-amino-2H-tetrazolyl and 5-methyl-1H-tetrazolyl radicals, the isomeric forms of said compound and the pharmaceutically acceptable salts of said compound.

34. A compound as claimed in claim 33, wherein $R_3$ represents a radical selected from the group consisting of a 1-tetrazolyl radical, a 5-amino-1H-tetrayolyl radical and a 5-methyl-1H-tetrayolyl radical.

35. A compound as claimed in claim 33, wherein X represents —N=C—.

36. A compound as claimed in claim 33, wherein R represents hydroxy.

37. A compound having the formula

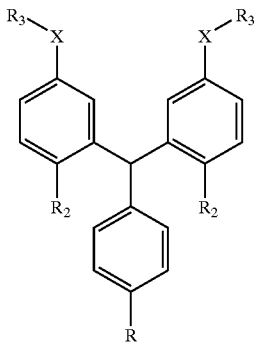

wherein X is a divalent linking moiety selected from the group of —CH=CH—, or —N=C—, the nitrogen of said divalent linking moiety being bound to $R_3$; R is a radical selected from the group of hydrogen, hydroxy, alkoxy, alkyl, halogen, nitro or alkoxy monosubstituted with a substituent selected from carboxyl, amino, monoalkylamino, dialkylamino or acetamido; $R_2$ is hydroxy; and $R_3$ is an unsubstituted heterocyclic radical selected from the group consisting of a 1-pyrazolyl radical, a 1-triazolyl radical, a 4-triazolyl radical, a 1-tetrazolyl radical, or a 2-tetrazolyl radical, or a substituted heterocyclic radical selected from the group consisting of 3-amino-4H-1,2,4-triazolyl, 5-amino-1H-1,2,4-triazolyl, 5-amino-2H-tetrazolyl and 5-methyl-1H-tetrazolyl radicals, the isomeric forms of said compound and the pharmaceutically acceptable salts of said compound.

38. A compound having the formula

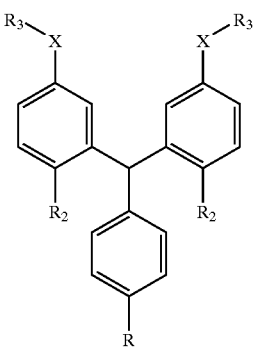

wherein X is a divalent linking moiety selected from the group of —CH=CH—, or —N=C—, the nitrogen of said divalent linking moiety being bound to $R_3$; R is a radical selected from the group of hydrogen, alkoxy, alkyl, halogen, nitro or alkoxy monosubstituted with a substituent selected from carboxyl, amino, monoalkylamino, dialkylamino or acetamido; $R_2$ is hydroxy; and $R_3$ is an unsubstituted heterocyclic radical selected from the group consisting of a 1-pyrazolyl radical, a 1-triazolyl radical, a 4-triazolyl radical, a 1-tetrazolyl radical, or a 2-tetrazolyl radical, or a substituted heterocyclic radical selected from the group consisting of 5-amino-1H-tetrazolyl, 3-amino-4H-1,2,4-triazolyl, 5-amino-1H-1,2,4-triazolyl, 5-amino-2-H-tetrazolyl and 5-methyl-1H-tetrazolyl radicals, the isomeric forms of said compound and the pharmaceutically acceptable salts of said compound.

\* \* \* \* \*

UNITED STATES PATENT AND TRADEMARK OFFICE
CERTIFICATE OF CORRECTION

PATENT NO.     : 6,495,580 B1
DATED          : November 12, 2003
INVENTOR(S)    : Nitz et al.

It is certified that error appears in the above-identified patent and that said Letters Patent is hereby corrected as shown below:

Column 22,
Line 45, "A pharmaceutical composition as claimed in claim 1," should read
-- A pharmaceutical composition as claimed in claim 28, --;

Column 23,
Line 19, "bound to $R_3$ R is" should read -- bound to $R_3$, R is --;
Line 35, "5-amino-1H-tetrayolyl radical" should read -- 5-amino-1H-tetrazolyl radical --;
Line 36, "5-methyl-1H-tetrayolyl radical" should read -- 5-methyl-1H-tetrazolyl radical --;

Column 24,
Line 55, please insert the following claim:
39. A method of treating biological materials that are susceptible to infection by, or infected or contaminated with a pneumovirus, said method comprising administering to said materials an effective amount of a compound as claimed in claim 1.

Signed and Sealed this

Twenty-seventh Day of April, 2004

JON W. DUDAS
*Acting Director of the United States Patent and Trademark Office*